United States Patent
Kumar et al.

US006846483B2

(10) Patent No.: US 6,846,483 B2
(45) Date of Patent: Jan. 25, 2005

(54) MICROBIAL COMPOSITION AND A PROCESS USEFUL FOR THE NEUTRALIZATION OF ALKALINE WASTEWATERS

(75) Inventors: Rita Kumar, Delhi (IN); Anil Kumar, Delhi (IN); Alka Sharma, Delhi (IN); Sharad Vishwanath Gangal, Delhi (IN); Santosh Dayaram Makhijani, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/867,367

(22) Filed: May 29, 2001

(65) Prior Publication Data

US 2002/0064864 A1 May 30, 2002

Related U.S. Application Data

(63) Continuation of application No. 09/160,422, filed on Sep. 25, 1998, now abandoned.

(51) Int. Cl.[7] ............................. A01N 63/00; C02F 3/00
(52) U.S. Cl. ................... 424/93.46; 210/601; 210/610; 210/611
(58) Field of Search ....................... 424/93.46; 210/601, 210/610, 611

(56) References Cited

U.S. PATENT DOCUMENTS

| | | | | |
|---|---|---|---|---|
| 4,052,262 A | * | 10/1977 | Horikoshi et al. | ........ 195/66 R |
| 4,511,657 A | * | 4/1985 | Colaruotolo et al. | ....... 435/253 |
| 5,565,348 A | | 10/1996 | Boyer et al. | ................. 435/221 |
| 5,707,851 A | | 1/1998 | Jones et al. | .............. 435/252.1 |

FOREIGN PATENT DOCUMENTS

| | | |
|---|---|---|
| JP | 06277693 | 10/1994 |
| JP | 09215996 | 8/1997 |

OTHER PUBLICATIONS

Boyer et al. "*Bacillus alcalophilus* subsp. halodurans subsp. nov.: an alkaline–amylase–producing, alkalophilic organism," 1973, Internation Journal of systematic bacteriology, vol. 23, No. 3, pp. 238–242.*

Boyer et al. "Extracellular Alkaline amylase from a Bacillus species," 1972, vol. 110, No. 3, pp. 992–1000.*

* cited by examiner

*Primary Examiner*—Shengjun Wang
(74) *Attorney, Agent, or Firm*—Merchant & Gould P.C.

(57) ABSTRACT

The invention relates to a microbial composition for the neutralization of alkaline waste waters by biological means and a method of neutralization of alkaline waste waters using a synergistic mixture of the bacterial strains of *Bacillus alkalophilus* and *Bacillus* sp.

1 Claim, No Drawings

MICROBIAL COMPOSITION AND A PROCESS USEFUL FOR THE NEUTRALIZATION OF ALKALINE WASTE-WATERS

This application is a continuation of application Ser. No. 09/160,422, filed Sep. 25, 1998, now abandoned, which application(s) are incorporated herein by reference.

FIELD OF THE INVENTION

The present invention relates to a microbial composition and a process for the preparation of the said microbial composition useful for the neutralization of alkaline waste-waters.

DESCRIPTION OF THE PRIOR ART

Rapid urbanization of developing countries as well as industrialization has adversely affected the environment, particularly with respect to water pollution. Water is polluted mainly by wastes generated through industrial processes, chemical agents from fertilizers & pesticides, silt from degraded catchments and traditional organic wastes. Waste-water generated from industries is a major cause of surface water pollution. Some of the waste-waterss from industrial processes pose a major problem for treatment as they are alkaline in nature. Industries producing alkaline waste-waters include textile industries, paper and pulp industries and many others. These alkaline waste-waters have a high pH ranging from 8.0–11.0. Since the pH of alkaline waste-waters is very high (more than 9), so it is not permissible to drain out these waste-waters as such.

Further, for the biological treatment of such waste-waters, prior neutralization is essential as most of the microbial strains present in activated sludge process work well near neutral pH. Therefore, alkaline waste-waters need to be first neutralized and then either sent to drainage or to treatment processes for further treatment.

The studies reveal that the neutralization of alkaline waste-waters is being done by purely chemical means where lots of acid is used which is often economically not feasible. Use of large quantities of acids is unsafe as it poses serious health hazards to the workers. There is no prior art proposal for the neutralization of alkaline waste-waters by biological means. Therefore, a microbial composition is formulated for the neutralization of alkaline waste-waters.

The alkalophilic bacteria used in the present invention are able to neutralize the alkaline environment and thus may find wide applications in industries emanating alkaline waste-waters.

The main advantages of the present invention are economy and safety. From economic point of view, the use of prepared microbial composition has advantages, as tonnes of acid is being used everyday to neutralize the alkaline waste-waters. Such a process becomes expensive to the extent that the industries find it economically non-feasible. A better alternative to the existing problem is to neutralize such waste-waters by biological means using the formulated microbial composition.

The utilization of acid in large quantities for the neutralization of waste-waters is also not safe for the industry as the strong acid has dangerous effect on the health of workers as well as on the industrial processes. Besides this, use of a large quantity of acid also increases the volume of industrial waste-waters to be drained out in the main stream.

For solving the aforementioned problem, the inventors have realized that there exists a need to provide an economic and safe process to neutralize the alkaline waste-waters which are emanating from different industries.

Alkalophilic bacteria used in present invention have been found to be adapted to the alkaline environment up to a pH 11.0. During the exponential phase, the growth rate immediately altered to the phenotypic characteristic of bacteria at higher pH indicating rapid adaptation. Due to such adaptation, the occurrence of the different pH optima is unusual and may reflect the operation of different limiting physiological systems at these pH values . The response of exponentially growing cultures to alteration in pH values in the medium indicates that these optima were not due to the presence of more than one genetically different variants. On the laboratory scale experiments, the microbial composition selected are able to neutralize alkaline medium as well as alkaline waste-water from textile industry. The microbial composition chosen for the invention produces more acid in presence of carbohydrates than without carbohydrates. Higher acid production in the presence of carbohydrates may be due to utilization of carbohydrates by bacteria as a source of carbon. Some industrial waste-waters may be rich in high carbohydrate content (e.g. starch) and may help in producing acid by using the available carbohydrates in the waste-waters. By using the alkalophilic microbial composition, the addition of sugar industry waste-waters (rich in carbohydrate content) in the alkaline waste-water (without carbohydrate content) may be advantageous for neutralization of these combined waste-waters.

OBJECTS OF THE INVENTION

The main object of the present invention is to provide a microbial composition and a process for the preparation of microbial composition useful for the neutralization of alkaline waste-waters.

Another object of the present invention is to provide a safe as well as economical process for the neutralization of alkaline waste-water. The formulated microbial composition of the present invention comprises of cultures of following bacteria: (a) *Bacillus alkalophilus* (b) *Bacillus* sp. The microbial composition is obtained by acclimatizing both the bacteria at higher pH, inoculating a suspension individually, incubating, mixing in equal proportions based on optical density and centrifuging. The resultant pellet is lyophilized to get a mixed powder of both the bacterial strains.

SUMMARY OF THE INVENTION

The present invention provides a process for the development of microbial composition of alkalophilic bacterial useful for the neutralization of alkaline waste-waters which is very economical and safe.

DETAILED OF THE INVENTION

The composition provided according to the present invention contained bacteria consisting of:

1. *Bacillus alkalophilus* CBTCC/Micro/8 (having characteristics similar to ATCC No.27647).
2. *Bacillus* sp. CBTCC/Micro/9 (having characteristics similar to ATCC No. 27557).

The alkalophilic bacteria used for the above stated composition were isolated from sewage having slight alkaline pH (7.5–8.0) by following the standard method. A selective medium, Alkaline Bacillus broth medium, was used for the isolation of alkalophilic bacteria. Alkaline Bacillus broth medium contained 10.0 gm glucose, 5.0 gm peptone, 5.0 gm yeast extract, 10.0 gm $K_2HPO_4$ and 0.2 gm $MgSO_4$ $7H_2O$ per liter. For solid medium, 20.0 gm agar was added. Aseptically added 100 ml of 10% sodium carbonate to the medium. The medium was sterilized at 120° C. for 20 min. The pH of alkaline *Bacillus* broth medium was adjusted to 8.0 to 11.0 using Tris-HCl buffer and NaOH—$Na_2CO_3$ buffer or $NaHCO_3$ $0Na_2CO_3$ buffer under sterile conditions. Sewage sample was diluted serially from $10^{-1}$ to $10^{-10}$. 0.1 ml of serially diluted sewage sample was streaked onto agar plates of the medium. Incubated the inoculated plates at 37° C. Several alkalophilic colonies were isolated and streaked on separate agar plates. The isolates were grown in broth medium of different pH values ranging between 8.0 to 11.0 for 24 hrs. at 37° C. The isolated pure cultures were used for further study.

The main characteristic features of *Bacillus alkalophilus* (CBTCC/Micro/8) used for the invention are:

*Bacillus alkalophilus* is endospore forming and Gram positive rod.

*Bacillus alkalophilus* is aerobic in nature.

*Bacillus alkalophilus* shows its optimum growth at 37° C.

*Bacillus alkalophilus* grows at high pH range i.e. 8.0 to 11.0 but not able to grow at neutral pH value. This shows its alkalophilic nature.

*Bacillus alkalophilus* produces acid in the presence of carbohydrates i.e. glucose and sucrose.

*Bacillus alkalophilus* is catalase positive.

*Bacillus alkalophilus* hydrolyses casein, gelatin and starch but unable to hydrolyse urea.

*Bacillus alkalophilus* is able to utilize citrate and propionate.

*Bacillus alkalophilus* is able to reduce methylene blue.

All the above characteristics of *Bacillus alkalophilus* used for the invention are similar to *Bacillus alkalophilus* corresponding to ATCC No. 27647.

The main characteristic features of *Bacillus* sp. (CBTCC/Micro/9) used for the invention are:

*Bacillus* sp. is endospore forming and Gram positive rod.

*Bacillus* sp. is aerobic in nature.

*Bacillus* sp. shows its optimum growth at 37° C.

*Bacillus* sp. grows at high pH range i.e. 8.0 to 11.0 but not able to grow at neutral pH value. This shows its alkalophilic nature.

*Bacillus* sp. Produces acid in the presence of carbohydrates i.e. glucose and sucrose.

*Bacillus* sp. is catalase positive.

*Bacillus* sp. hydrolyses casein, gelatin and starch but unable to hydrolyse urea.

*Bacillus* sp. is unable to utilize citrate.

*Bacillus* sp. is able to reduce nitrate.

All the above characteristics of *Bacillus* sp. used for the invention are similar to *Bacillus* general having characteristics similar to ATCC No. 27557.

The microbial composition of the present invention is useful for the neutralization of alkaline waste-waters.

The microbial composition is formulated by inoculating the individual strains of the above mentioned bacteria separately in Alkaline *Bacillus* broth medium containing 10.0 gm glucose, 5.0 gm peptone, 5.0 gm yeast extract, 10.0 gm $K_2HPO_4$ & 0.2 gm $MgSO_4$ $7H_2O$ per liter. For solid media 20.0 gm agar was added. Aseptically added 100 ml of 10% sodium carbonate to the medium. The medium was sterilized at 120° C. for 15 min. Morphological properties and taxonomic characteristics of bacteria were investigated according to the Bergey's Manual of Determinative Bacteriology. These cultures were grown in two different media i.e. Nutrient Broth (NB) medium and Modified Tryptone Soya Broth (TSB) medium for obtaining better growth. Nutrient broth medium contained 1.0 gm beef extract, 2.0 gm yeast extract, 5.0 gm peptone, 5.0 gm sodium chloride per liter at pH about 7.0. The cultures were grown by inoculating them in the same medium but at different pH, ranging from 8.0 to 11.0 . Tris-HCl buffer was used for adjusting the pH upto 9.0. Buffer $NaHCO_3$—$Na_2CO_3$ was used to adjust pH values from 9.0 to 11.0. Modified Tryptone Soya Broth medium comprised of 5.6 gm pancreatic digest of casein, 1.6 gm sodium chloride, 0.83 gm dibasic potassium phosphate, 0.83 gm dextrose per liter. Different pH values of TSB medium were obtained by using Tris-HCl buffer and NaOH—$NaHCO_3$ or $NaHCO_3$—$Na_2CO_3$ under sterile conditions. Compared the growth of bacterial strains in NB medium and modified TSB medium. On the basis of better growth of bacterial strains, modified TSB medium was selected for further study. The bacterial strains unable to grow at pH 11.0 were acclimatized at pH 11.0. Production of acid by acclimatized bacteria was observed in modified NB medium. Modified NB medium contained 1.5 gm peptone, 5.3 gm NaCl, 0.12 gm yeast extract, 0.016 gm beef extract, 0.3 gm $K_2HPO_4$ per liter. The different pH value ranging from 9.0 to 11.0 of modified NB medium was adjusted by using NaOH—$NaHCO_3$ buffer or $NaHCO_3$—$Na_2CO_3$ under sterile conditions. The Bacterial were grown in modified Nutrient Broth medium for 2 to 5 days. The acid produced by the bacteria was observed by measuring the decrease in pH of the incubated media waste-waters with the help of a pH electrode at different time intervals. A dye, phenol red indicator, was added to the media to observe the change in colour of the media due to acid production. Change in colour of phenol red from red to orange and orange to yellow was also an indication of acid production by the bacteria.

Accordingly, the present invention provides a microbial composition comprising a synergistic mixture of at least following two bacterial strains present in about equal proportion for the neutralization of alkaline waste-waters:

a. *Bacillus alkalophilus*
b. *Bacillus* sp.

The invention further provides a process for the preparation of microbial composition useful for the neutralization of alkaline waste-waters which comprises:

The invention further provides a process for the preparation of microbial composition useful for the neutralization of alkaline waste-waters which comprises:

a) isolating the bacterial strains *Bacillus alkalophilus* and *Bacillus* sp. from sewage by standard method;

b) inoculating the said individual bacterial strains in an Alkaline *Bacillus* broth medium containing $MgSO_4$;

c) growing the said individual bacterial strains for 16–24 hrs;

d) inoculating the said individual bacterial strains from step (c) in a modified Tryptone Soya Broth medium, having original pH value about 7.0, the said pH value of the medium being adjusted to different pH values ranging between 8.0–11.0, using Tris-HCl buffer and NaOH—$Na_2CO_3$ buffer or $NaHCO_3$—$Na_2CO_3$ buffer under sterile conditions;

e) growing the said individual bacterial strains obtained from step (d) in modified Tryptone Soya Broth medium for 16–24 hrs. at different pH values ranging from 8.0–11.0 to select the bacterial strains growing at pH 11.0 and the remaining bacterial strains unable to grow at pH 11.0 being acclimatized at pH 11.0;

f) inoculating the said selected acclimatized individual bacterial trains from step (e) in a modified Nutrient Broth medium, having pH values about pH 7.0, the said pH being adjusted to different pH values ranging from 9.0–11.0 using NaOH—$Na_2CO_3$ buffer or $NaHCO_3$—$Na_2CO_3$ buffer under sterile conditions;

g) adding a dye, phenol red indicator and optionally 1% carbohydrate to the said inoculated medium of individual bacterial strains obtained from step (f) to observe the change in colour for acid production and to identify the acid producing strains at pH 9.0–11.0;

h) growing the said inoculated bacterial strains obtained from step (g) for a period of at least 2 days and thereafter observing acid production by the change in colour of phenol red in the said medium from red to orange, orange to yellow and by measuring the decrease in pH of the said medium;

i) selecting the acid producing bacterial strains at pH 11.0;

j) mixing the said selected bacterial strains from step (i) to obtain mixed bacterial suspension;

k) centrifuging the mixed suspension of bacterial strains obtained from step j) at 8,000–12,000 rpm to obtain pellet;

l) washing the obtained pellet from step (k) by suspending the pellet in triple distilled water and recentrifuging at 8,000–12,000 rpm;

m) collecting the pellet from step (l) and lyophilizing the obtained pellet to store at 1 to 4° C. for longer use;

The invention further provides a method for the neutralization of alkaline waste-waters using a microbial composition comprising a synergistic mixture of at least following two bacterial strains present in about equal proportion for the neutralization of alkaline waste-waters:

a. *Bacillus alkalophilus*
b. *Bacillus* sp.;

the said method comprising:

a) reconstituting lyophilized bacterial powder by adding 50 ml distilled water;

b) adding 10% reconstituted bacterial strains in alkaline medium and alkaline waste-waters containing phenol red indicator and optionally 1% carbohydrate;

c) observing acid production by the change in colour of phenol red in modified Nutrient Broth medium and in the alkaline waste-waters from red to orange, orange to yellow and by measuring the decrease in pH of the said medium as well as of alkaline waste-waters to neutral after a period of at least 2 days;

In an embodiment of the present invention, the formulated microbial composition is obtained by inoculating a suspension of the following bacterial strains: a) *Bacillus alkalophilus* & b) *Bacillus* sp., individually.

In an another embodiment of the present invention, the individual strains of the above mentioned bacteria are inoculated separately in NB medium and modified Trytone Soya Broth medium having original pH about 7.0, adjusted to different pH values ranging from pH 8.0 to 11.0.

In a still another embodiment of the present invention, pH of Nutrient Broth medium is adjusted using Tris-HCl buffer and NaOH—$Na_2CO_3$ buffer or $NaHCO_3$—$Na_2CO_3$ buffer.

In one of the embodiments of the present invention, pH of modified Tryptone Soya Broth medium is adjusted using Tris-HCl buffer and NaOH—$Na_2CO_3$ buffer or $NaHCO_3$—$Na_2CO_3$ buffer.

In an embodiment of the present invention, the incubation of bacterial strains is carried out by gentle agitation at approximately 75–100 rpm In one of the embodiments of the present invention, the growth of incubated bacterial strains is carried out at a temperature ranging between 35° C.–40° C. for a period of 16–24 hrs.

In an another embodiment of the present invention, the growth of the bacterial strains is compared in Nutrient Broth medium and modified Tryptone Soya Broth medium by observing optical density at 650 nm.

In a further embodiment of the present invention, the modified Tryptone Soya Broth medium supporting the growth of the individual bacterial strains is selected for further study.

In an another embodiment of the present invention, the individual bacterial strains are inoculated in modified Tryptone Soya Broth medium having original pH value 7.0 which is adjusted to different pH values ranging from 8.0 to 11.0 to select the bacterial strains growing at higher pH values. The bacterial strains, unable to grow at pH 11.0 were acclimatized upto pH 11.0.

In a still another embodiment of the present invention, the selected acclimatized bacterial strains are inoculated in modified Nutrient Broth medium having original pH value 7.0 which is adjusted to different pH values ranging from 9.0 to 11.0 using NaOH—$Na_2CO_3$ buffer or $NaHCO_3$—$Na_2CO_3$ under sterile conditions to observe acid production.

In one of the embodiments of the present invention, a dye, phenol red indicator and 1% glucose and 1% sucrose are added into modified Nutrient Broth medium to measure the change in colour and decrease in pH of the medium.

In an another embodiment of the present invention, acid production is observed by bacterial strains by change in colour from red to orange, orange to yellow and measuring the decrease in pH of modified Nutrient Broth medium.

In a still another embodiment of the present invention, the suspension of the individual selected bacterial strains are mixed thoroughly in equal proportions based on optical density.

In one of the embodiments of the present invention, the mixed suspension of the bacterial strains is centrifuged at appropriate rpm preferably at 8,000–12,000 rpm for a period of approximately 20–30 minutes.

In an another embodiment of the present invention, the resultant pellets of mixed bacterial strains are washed by dissolving in an appropriate quantity of distilled water and recentrifuging at an appropriate rpm in the range of 8,000–12,000 rpm for a period of approximately 20–30 minutes at a temperature less than or equal to 4° C.

In a still another embodiment of the present invention, the mixed microbial composition is suspended into modified Nutrient Broth medium and alkaline waste-waters of textile industry separately having different pH values ranging from 9.0 to 11.0. In an another experimental setup, 1% glucose as well as 1% sucrose are also added separately into the medium as well as in the alkaline waste-waters having different pH values ranging from 9.0 to 11.0 to provide the additional carbon source to both the bacteria used in the study which lead to more acid production by the bacteria.

In a yet another embodiment of the present invention, phenol red indicator, a dye used as a indicator of acid production, is added to modified Nutrient Broth medium as welt as alkaline waste-waters to observe the change in colour due to acid production.

In a further embodiment of the present invention, all the suspensions of bacterial strains growing at different pH values containing different carbohydrates as well as phenol red indicator are incubated for 2–5 days.

In one of the embodiments of the present invention, acid production is observed by the change in colour of phenol red from red to orange, orange to yellow and by measuring the decrease in pH of the modified Nutrient Broth medium as well as of alkaline waste-waters after 2–7 days of incubation time.

In a another embodiment of the present invention, the prepared microbial composition is useful for the neutralization of alkaline waste-waters with the optional addition of 1% cabohydrates.

The invention is illustrated with the help of the following examples and should not be construed to limiting the scope of the invention.

EXAMPLE 1

Two loops from agar plates of *Bacillus alkalophilus* and *Bacillus* sp. were inoculated separately in plates of NB medium and modified TSB medium containing 2% agar having original pH about 7.0 which is adjusted to different pH values ranging from 8.0–11.0. For adjusting the different pH values of NB medium, different buffers were used. Tris-HCl buffer was used for adjusting pH values upto 9.0, whereas, $Na_2CO_3$—$NaHCO_3$ buffer was used to adjust the pH values ranging from 9.0–11.0. Different pH values of modified TSB medium were adjusted using Tris-HCl and NaOH—$NaHCO_3$ buffers under sterile conditions. Both the bacterial cultures inoculated at different pH values were incubated at 37° C. for 24 hrs in an incubator shaker at 75 rpm. Growth of individual bacterial cultures in both the media was observed at different pH values.

Table 1 shows the growth of both the bacteria at different pH values ranging from 8.0–11.0.

TABLE 1

Comparison of growth of alkalophilic bacterial cultures on agar plates in NB medium and modified TSB medium

| | NB medium | | TSB medium Modified | |
|---|---|---|---|---|
| pH values | Bacillus alkalophilus | Bacillus sp. | Bacillus alkalophilus | Bacillus sp. |
| 8.0 | + | + | ++ | ++ |
| 8.5 | + | + | +++ | +++ |
| 9.0 | ++ | ++ | ++++ | ++++ |
| 9.5 | − | − | +++ | +++ |
| 10.0 | − | − | ++ | ++ |
| 10.5 | − | − | ++ | ++ |
| 11.0 | − | − | ++ | ++ |

+ very poor growth
++ poor growth
+++ good growth
++++ very good growth

It was observed that both the bacteria showed better growth in the plates of modified TSB medium containing agar than NB medium containing agar (Table 1). This may be due to better buffering capacity and optimum ingredients present in modified TSB containing agar for the growth of both the bacteria. So, modified TSB is selected for further experiment.

EXAMPLE 2

Two loops from agar plates of *Bacillus alkalophilus* and *Bacillus* sp. were inoculated separately in 500 ml of modified TSB medium having original pH about 7.0 which is adjusted to different pH values ranging from 8.0–11.0. Different pH values of modified TSB medium were adjusted using Tris-HCl and NaOH—$NaHCO_3$ buffers under sterile conditions. Both the bacterial cultures inoculated at different pH values were incubated at 37° C. for 24 hrs. in an incubator shaker at 100 rpm. Growth of individual bacterial cultures in terms of optical density in modified TSB medium was observed at different pH values.

Table 2 represents the growth of both the bacteria at different pH values ranging from 8.0–11.0.

TABLE 2

Growth of the alkalophilic bacteria in terms of optical density (OD) at 650 nm at different pH values in modified TSB medium

| | Optical Density of bacteria at 650 nm | |
|---|---|---|
| pH values | Bacillus alkalophilus | Bacillus sp. |
| 8.0 | 0.372 | 0.421 |
| 8.5 | 0.380 | 0.552 |
| 9.0 | 0.512 | 0.586 |
| 9.5 | 0.384 | 0.489 |
| 10.0 | 0.299 | 0.385 |
| 10.5 | 0.294 | 0.343 |
| 11.0 | 0.281 | 0.293 |

It was observed that both alkalophilic cultures showed optimum growth at pH 9.0. This represents the facultative nature of micro-organisms used for the study, which states that microbes show optimal growth at pH 9.0 or above but which can grow well in the near neutral pH range. Acclimatization of both the bacterial strains is required at higher pH values.

EXAMPLE 3

Two loops from agar plates of *Bacillus alkalophilus* and *Bacillus* sp. were inoculated separately in 500 ml of modified TSB medium of about pH 7.0. The inoculated bacterial cultures were incubated at 37° C. for 24 hrs. in an incubator shaker at 75 rpm Optical density of both the bacterial cultures was observed.

Acclimatization of both the bacterial strains to different pH values in the modified TSB medium was accomplished by subculturing the bacterial cultures a number of times at pH values in increasing order. Once the optimum growth was obtained at pH 11.0, 500 ml of growth suspension was centrifuged at 8,000 rpm and the pellet after washing was suspended in carbonate buffer of pH 11.0. The suspended pellet was freeze dried to obtain bacterial powder of both bacterial strains, individually. The lyophilized bacterial powder was stored at about 1° C.

EXAMPLE 4

Once *Bacillus alkalophilus* and *Bacillus* sp. were acclimatized at pH 11 both the bacterial cultures were inoculated in modified NB medium of different pH values ranging from pH 8.0–11.0. To observe acid production by both alkalophilic bacterial strains, phenol red indicator was added to the medium. Both the bacterial strains were incubated at 37° C. for 2–5 days in an incubator shaker at 75 rpm Change in the colour of phenol red indicator from red to orange and orange to yellow was observed which is an indicator of acid production by bacteria. The acid production by bacterial strains was also observed by measuring the pH of the incubated modified NB medium at different time intervals.

Table 3 indicates the acid production by both the bacterial strains at different pH values. The acid production was observed by measuring the decrease in pH of the medium.

TABLE 3

Change of pH in modified NB medium by alkalophilic bacteria after two and five days incubation

| Alkalophilic bacteria | Original pH of the medium | pH of the medium after 2 days incubation | pH of medium after 5 days incubation |
|---|---|---|---|
| Bacillus alkalophilus | 9.07 | 7.91 | 7.10 |
|  | 9.53 | 8.57 | 7.85 |
|  | 9.96 | 9.07 | 8.64 |
|  | 10.48 | 9.75 | 9.30 |
| Bacillus sp. | 9.07 | 8.09 | 7.54 |
|  | 9.53 | 8.69 | 8.08 |
|  | 9.96 | 9.17 | 9.28 |
|  | 10.48 | 9.94 | 9.95 |

The overall change in pH was observed in the range of 0.5 to 2.0 pH units. This change in pH of the medium may possibly be attributed to the production of an enzyme amino acid deaminase which tends to decrease the alkalinity of the media.

EXAMPLE 5

Both acclimatized bacterial cultures were used for acid production in the presence of different sources of carbohydrates. For this, 1% sucrose and 1% glucose were added in modified NB medium separately containing phenol red indicator. The change in colour of medium as well as decrease in pH was observed for both bacterial cultures at different pH values ranging pH 9.0–11.0.

Table 4 and 5 represent change in pH of medium by alkalophilic bacterial strains in the presence of 1% sucrose and 1% glucose respectively, after 2 and 5 days incubation.

TABLE 4

Change of pH in modified NB medium containing sucrose by alkalophilic bacteria after two and five days incubation

| Alkalophilic bacteria | Original pH of the medium | pH of the medium after 2 days incubation | pH of medium after 5 days incubation |
|---|---|---|---|
| Bacillus alkalophilus | 9.02 | 5.61 | 6.00 |
|  | 9.58 | 7.81 | 6.75 |
|  | 9.90 | 8.22 | 7.21 |
|  | 10.42 | 8.92 | 7.80 |
| Bacillus sp. | 9.02 | 6.86 | 5.12 |
|  | 9.58 | 7.74 | 6.61 |
|  | 9.90 | 8.22 | 7.05 |
|  | 10.42 | 8.89 | 7.89 |

Presence of sucrose supported the growth of both the bacterial strains and enhanced the acid production by both the bacteria. After 2–5 days of incubation, acid production by bacteria was indicated by the shift in pH values in the range of 1.5–4.0 pH units by both the cultures.

TABLE 5

Change of pH in modified NB medium containing glucose by alkalophilic bacteria after two and five days incubation

| Alkalophilic bacteria | Original pH of the medium | pH of the medium after 2 days incubation | pH of medium after 5 days incubation |
|---|---|---|---|
| Bacillus alkalophilus | 9.25 | 5.65 | 5.39 |
|  | 9.63 | 7.48 | 6.20 |
|  | 9.98 | 8.40 | 6.92 |
|  | 10.64 | 9.09 | 7.72 |
| Bacillus sp. | 9.25 | 7.34 | 5.67 |
|  | 9.63 | 8.02 | 6.68 |
|  | 9.98 | 8.47 | 8.02 |
|  | 10.64 | 9.14 | 8.80 |

There was a significant change in the original pH of the medium in the range of 1.5–4.0 pH units by both the bacteria. The decrease in pH of the medium was also indicated by colour change of phenol red from red to orange to orangish yellow to yellow. The results of change in pH of medium in the presence of glucose were comparable with the results of change in original pH in the presence of sucrose.

From Table 4 and 5, it was concluded that presence of carbohydrates in the medium enhanced the acid production.

EXAMPLE 6

Alkaline waste-waters (pH upto 12.0) from textile industry was selected for neutralization studies by using both the alkalophilic bacterial strains. The original pH of the waste-waters was measured.

For the neutralization of alkaline waste-waters by biological means, the acclimatized and lyophilized culture of Bacillus sp. was reconstituted in 50 ml sterile triple distilled water, overnight. A 10% concentration of reconstituted culture was added in alkaline waste-waters for neutralization. The alkaline waste-waters containing bacterial culture was incubated at 37° C. for a period of 7 days in an incubator shaker at 100 rpm.

Table 6 represents the neutralization of alkaline waste-waters from textile industry using Bacillus sp. The change in original pH of waste-waters was observed after 3 and 7 days incubation time.

TABLE 6

Neutralization of alkaline waste-waters from textile industry by Bacillus sp.

| Original pH of waste-water | After 3 days incubation | | After 7 days incubation | |
|---|---|---|---|---|
|  | pH | change in pH | pH | change in pH |
| 10.67 | 10.40 | 0.27 | 9.75 | 0.92 |
| 11.57 | 11.21 | 0.36 | 10.72 | 0.85 |
| 9.88 | 9.64 | 0.24 | 8.91 | 0.97 |
| 12.01 | 11.50 | 0.51 | 10.95 | 1.06 |
| 9.65 | 9.20 | 0.45 | 8.75 | 0.90 |

The overall change in original pH of the waste-waters was observed in the range of 0.24–1.06 units.

EXAMPLE 7

The neutralization of alkaline waste-waters of textile industry was carried out using acclimatized and lyophilized culture of Bacillus alkalophilus. The lyophilized powder of Bacillus alkalophilus was reconstituted in 50 ml sterile triple distilled water, overnight. A 10% concentration of reconstituted culture was added in alkaline waste-waters for neutralization. The alkaline waste-waters containing bacterial culture was incubated at 37° C. for a period of 7 days in an incubator shaker at 100 rpm Table 7 represents the neutralization of alkaline waste-waters from textile industry using *Bacillus alkalophilus*. The change in original pH of waste-waters was observed after 3 and 7 days incubation time.

TABLE 7

Neutralization of alkaline waste-waters from textile industry by *Bacillus alkalophilus*

| Original pH of waste-water | After 3 days incubation | | After 7 days incubation | |
|---|---|---|---|---|
| | pH | change in pH | pH | change in pH |
| 10.67 | 10.36 | 0.31 | 9.79 | 0.88 |
| 11.57 | 11.32 | 0.25 | 10.83 | 0.74 |
| 9.88 | 9.59 | 0.29 | 8.96 | 0.92 |
| 12.01 | 11.58 | 0.43 | 10.98 | 1.03 |
| 9.65 | 9.27 | 0.38 | 8.69 | 0.96 |

The overall change in original pH of the waste-waters using *Bacillus alkalophilus* was observed in the range of 0.25–1.03.

EXAMPLE 8

Bacterial cultures of *Bacillus alkalophilus* and *Bacillus* sp. acclimatized at pH 11.0 were obtained individually as described in Example 3. The acclimatized culture suspensions of both the individual bacterial strains of different pH were mixed in equal proportions based on optical density. The resultant growth suspension was centrifuged at 10,000 rpm for 30 minutes. The pellet was collected and washed with triple distilled water. Recentrifuged the mixed suspension at 12,000 rpm for 20 minutes. The pellet was collected and lyophilized. The lyophilized bacterial powder was stored at 4° C.

EXAMPLE 9

The acclimatized and lyophilized mixed bacterial powder of *Bacillus alkalophilus* and *Bacillus* sp. were reconstituted in 50 ml sterile triple distilled water overnight. The mixed reconstituted bacterial culture was used for the neutralization of alkaline waste-waters of textile industry. Three different sets of alkaline waste-waters were prepared to observe the acid production. In the first set, 10% of the mixed reconstituted bacterial suspension was added in the waste-waters. In the subsequent two sets, 10% of the mixed reconstituted bacterial suspension was added in waste-waters containing 1% glucose and 1% sucrose, respectively. All the three sets were incubated at 37° C. for a period of 7 days in an incubator shaker at 75 rpm Acid production by microbial composition was observed in all the three sets after 2, 4 and 7 days of incubation period.

Table 8 represents neutralization of alkaline waste-waters from textile industry by a microbial composition of alkalophilic bacteria in the presence as well as absence of carbohydrates.

TABLE 8

Neutralization of alkaline waste-waters from textile industry by alkalophilic microbial composition

| Alkaline waste-water | Original pH of waste-water | After 2 days incubation | | After 4 days incubation | | After 7 days incubation | |
|---|---|---|---|---|---|---|---|
| | | pH | change in pH units | pH | change in pH units | pH | change in pH units |
| Without carbo-hydrate | 10.67 | 10.52 | 0.15 | 10.14 | 0.53 | 9.65 | 1.02 |
| | 11.57 | 11.35 | 0.22 | 11.12 | 0.45 | 10.62 | 0.95 |
| | 9.88 | 9.76 | 0.12 | 9.40 | 0.48 | 8.90 | 0.98 |
| | 12.01 | 11.83 | 0.18 | 11.39 | 0.62 | 10.88 | 1.13 |
| | 9.65 | 9.42 | 0.23 | 9.13 | 0.52 | 8.79 | 0.86 |
| With 1% sucrose | 10.67 | 8.60 | 2.07 | 8.14 | 2.53 | 7.94 | 2.73 |
| | 11.57 | 9.32 | 2.25 | 8.95 | 2.62 | 8.69 | 2.88 |
| | 9.88 | 7.75 | 2.13 | 7.50 | 2.38 | 7.36 | 2.52 |
| | 12.01 | 9.82 | 2.19 | 9.43 | 2.54 | 8.96 | 3.05 |
| | 9.65 | 7.63 | 2.02 | 7.26 | 2.39 | 7.02 | 2.63 |
| With 1% glucose | 10.67 | 8.30 | 2.37 | 7.61 | 3.06 | 7.24 | 3.43 |
| | 11.57 | 8.96 | 2.61 | 8.24 | 3.33 | 7.83 | 3.74 |
| | 9.88 | 7.72 | 2.16 | 7.12 | 2.76 | 6.81 | 3.07 |
| | 12.01 | 9.57 | 2.44 | 8.86 | 3.15 | 8.35 | 3.66 |
| | 9.65 | 7.59 | 2.06 | 7.01 | 2.64 | 6.65 | 3.00 |

A significant change was observed in the original pH of the waste-waters of textile industry after regular time intervals. Decrease in original pH of waste-waters was less in the absence of carbohydrates as compared to that with carbohydrates. Among carbohydrates, original pH decreased markedly in the presence of 1% glucose in comparison to 1% sucrose.

From the examples explained above it is clear that neutralization of alkaline medium as well as alkaline waste-waters emanating from textile industry using microbial composition is a safe as well as economical biological process.

Advantages

1. The neutralization of alkaline waste-waters using microbial composition is a very economic biological process because tonnes of acid is being used everyday to neutralize the alkaline waste-waters. Such a process becomes expensive to the extent that the industries find it economically non-feasible. A better alternative to the existing problem is to neutralize such waste-waters by biological means using prepared microbial composition which will decrease the cost for the neutralization process drastically.
2. The neutralization of alkaline waste-waters by biological means is quite safe process as the utilization of acid in large quantities for the neutralization of waste-waters is not safe for the industry as the strong acid has dangerous effect on the health of workers as well as on the industrial processes. Besides this, use of a large quantity of acid also increases the volume of industrial waste-waters to be drained out in the main stream. The use of large quantities of acid can also be a reason for explosion hazard.

We claim:

1. A process for the preparation of microbial composition useful for the neutralization of alkaline textile industry waste-waters comprising:
    (a) inoculating the bacterial strains *Bacillus alkalophilus* CBTCC/Micro/8 MTCC 5092 and *Bacillus* sp. CBTCC/Micro/9 MTCC 5093 an Alkaline Bacillus broth medium containing $MgSO_4$;
    (b) growing said individual bacterial strains for 16–24 hrs;
    (c) inoculating said individual bacterial strains grown in step (b) in a modified Txyptone Soya Broth medium, having original pH value about 7.0, said pH value of the medium being adjusted to different pH values ringing between 8.0–11.0, using Tris-HCl buffer and NaOH—Na$_2$CO$_3$ buffer or NaHCO$_3$—Na$_2$CO$_3$ buffer tinder sterile conditions;

(d) growing said individual bacterial strains obtained from step (c) in modified Tryptone Soya Broth medium for 16–24 hours at different pH values ranging from 8.0–11.0 to select the bacterial strains growing at pH 11.0 and the remaining bacterial strains unable to grow at pH 11.0 being acclimatized at pH 11.0;

(e) inoculating said selected acclimatized individual bacterial strains from step (d) in a modified Nutrient Broth medium, having pH values about pH 7.0, said pH being adjusted to different pH values ranging from 9.0–11.0 using NaOH—Na$_2$CO$_3$ buffer or NaHCO$_3$—Na$_2$CO$_3$ buffer under sterile conditions;

(f) adding a dye, phenol red indicator and optionally 1% carbohydrate to said inoculated medium of individual bacterial strains obtained from step (f) to observe the change in colour for acid production and to identify the acid producing strains at pH9.0–11.0;

(g) growing said inoculated bacterial strains obtained from step (g) for a period of at least 2 days and thereafter observing acid production by the change in colour of phenol red in said medium from red to orange, orange to yellow and by measuring the decrease in pH of said medium;

(h) selecting the acid producing bacterial strains at pH 11.0;

(i) mixing said selected bacterial strains from step (h) to obtain mixed bacterial suspension;

(j) centrifuging the mixed suspension of bacterial strains obtained from step (j) at 8,000–12,000 rpm to obtain pellet;

(k) washing the obtained pellet from step (j) by suspending the pellet in triple distilled water and re-centrifuging at 8,000–12,000 rpm; and (l) collecting the pellet from step (k) and lyophilizing the obtained pellet to store at 1 to 4° C. for longer use.

* * * * *